United States Patent [19]

Dugas et al.

[11] Patent Number: 5,246,701
[45] Date of Patent: Sep. 21, 1993

[54] METHOD FOR INHIBITING PRODUCTION OF IGE BY USING IL-9 INHIBITORS

[75] Inventors: Bernard Dugas, Orsay, France; Catherine Druez, Sint-Stevens-Woluwe, Belgium; Pierre Braquet, Garches; Jean M. Mencia-Huerta, Paris, both of France; Catherine Uyttenhove, Chaumont Gistoux, Belgium; Jean-Christophe Renauld, Brussels, Belgium; Jacques Van Snick, Kraainem, Belgium

[73] Assignees: Ludwig Institute for Cancer Research, New York, N.Y.; Department d'Immunologie Institut Henri Beaufour, Les Ulis, France

[21] Appl. No.: 807,260

[22] Filed: Dec. 13, 1991

Related U.S. Application Data

[62] Division of Ser. No. 593,238, Oct. 5, 1990, Pat. No. 5,132,109.

[51] Int. Cl.$^5$ .................. A61K 45/05; A61K 39/00; A61K 37/10; A61K 37/00
[52] U.S. Cl. .................. 424/85.8; 424/85.2; 514/8; 514/21; 530/388.22; 530/388.23
[58] Field of Search .............. 424/85.8, 85.2; 514/8, 514/21; 530/388.22, 388.23

[56] References Cited

U.S. PATENT DOCUMENTS 4,578,335  3/1986  Urdal et al. .................. 435/68
5,116,951  5/1992  Druez et al. .................. 530/395

FOREIGN PATENT DOCUMENTS

WO89/09621  10/1989  PCT Int'l Appl. .
WO91/08774  6/1991  PCT Int'l Appl. .

OTHER PUBLICATIONS

Mosley et al. (1989) Cell 59:335-348.
Hultner et al. (1990) Eur. J. Immunol. 20(6):1413-1416.
Dugas et al. (1990) Lymphokine Res. 9(4):572.
Druez et al. (Oct. 15, 1990) J. Immunol. 145(8):2494-2499.
Knight, "Allergy: Big Market, Big Risks": Bio/Technology 8: 717-719 (1990).
Fernandez-Botran et al., Proc. Natl. Acad. Sci. 87: 4202-4206 (Jun. 1990).
Sadick et al., J. Exp. Med. 171: 115-127 (Jan. 1990).
Henzel et al., J. Exp. Med. 169: 59-72 (Jan. 1989).
Coffman et al., Science 245: 08-310 (Jul. 21, 1989).
Aggarwal et al., Clinical Research (Blackwell), 1992, p. 113.

Primary Examiner—Robert A. Wax
Assistant Examiner—Keith D. Hendricks
Attorney, Agent, or Firm—Felfe & Lynch

[57] ABSTRACT

A method for inhibiting production of IgE, and a method for enhancing production of IgG are taught. The methods are linked to the role of interleukin 9 in antibody production. Specifically, production of IgG is potentiated by administering either to a subject or a cell culture a combination of interleukin 4 and interleukin 9. Production of IgE is inhibited by administering an amount of an interleukin 9 inhibitor to a subject.

8 Claims, 3 Drawing Sheets

METHOD FOR INHIBITING PRODUCTION OF IGE BY USING IL-9 INHIBITORS

This application is a division of Ser. No. 593,238 filed Oct. 5, 1990, now U.S. Pat. No. 5,132,109.

FIELD OF THE INVENTION

This invention relates to modulation of antibody responses in animals, including humans. More particularly, it relates to the stimulation of IgG production and the suppression of IgE production via manipulation of a mechanism related to both of these.

BACKGROUND AND PRIOR ART

The role of cytokines in immunological processes has now been recognized to be important and complex. A recent review article by Whicher et al., Clin. Chem. 36(7): 1269–1281 (1990), the disclosure of which is incorporated by reference herein, nicely summarizes what is known about the various cytokines and growth factors, including interleukins 1 through 8. Sources for these molecules, as well as their target cells are described. Of particular relevance to this disclosure are interleukin 4 ("IL-4" hereafter), and a cytokine not discussed in the review article, but know to the art, interleukin-9 ("IL-9" hereafter).

IL-4 is derived from T cells and mast cells, and targets T cells, B cells, macrophages/monocytes and mast cells. In particular, as Whicher points out at page 1274, IL-4 has a major role in the allergic response, following its release by activator $TH_2$ cells. The IL-4 molecule is involved in "Ig switching", i.e., the change to production of different types of Ig by B cells. This cytokine influences a switch toward production of IgE and IgA. See Yokota et al., Immunol. Rev. 102: 137–187 (1988).

IL-4's involvement in the allergic response is discussed in some detail by Knight, Bio/Technology 8: 717–719 (1990), the disclosure of which is incorporated by reference. The reference discusses, inter alia, the possibility of "short-circuiting" the allergic response by administering a soluble receptor of IL-4 to an afflicted subject. Both natural and recombinant forms of the receptor are available, but the latter type cannot bind to cells because it lacks a portion of the complete molecule. Nonetheless, it binds to the IL-4 molecule, preventing the stimulus leading to Ig switching in B cells.

This approach, i.e., that of using a soluble receptor for a cytokine so as to impact its normal effect, is demonstrated in the scientific literature. Fanslow, et al., Science 248: 739–741 (May 11, 1990) discuss the use of soluble IL-1 receptors, as well as antibodies which bind to this cytokine and suggests their use to mediate IL-1 related disorders. Smith, et al., Science 248 1019–1023 (May 25, 1990) discusses the role of soluble receptors for tumor necrosis factor (TNF) and potential value in therapeutic environments. The above referenced disclosures are incorporated by reference herein. In fact, soluble IL-1 receptor has been reported to inhibit rejection of heart transplants, and is suggested as being useful in treating diseases such as rheumatoid arthritis and multiple sclerosis where stimulation by IL-1 is involved. See Kolata, "Test Drug Blocks Rejection of New Hearts In Mice", New York Times, May 11, 1990.

Fairly recent work has identified a new member of the interleukin family, the molecule referred to by Hültner, et al., in Eur. J. Immunol. 20: 1413 (1990), as interleukin 9. This paper, the disclosure of which is incorporated by reference herein, sets forth research which shows, inter alia, that the molecules previously known as P40 (Uyttenhove, et al., PNAS 85: 6934 (1988)), and TCGFIII (Schmitt, et al., Eur. J. Immunol. 19: 2167 (1989)), as well as by Yang, et al., Blood 74: 1990 (1989), and Renauld, et al., Cytokine 2: 9 (1990), are the same. All of the foregoing papers are incorporated by reference herein. This molecule has been shown to possess many properties, including the ability to support the growth of helper T cell clones and mucosal mast cells. The latter are known to be involved in regulation of type I hypersensitivity reactions.

Druez, et al., J. Immunol. Oct. 15, 1990 (in press), the disclosure of which is incorporated by reference, and U.S. Ser. No. 585,229, filed Sep. 19, 1990, the disclosure of which is incorporated by reference herein describe the discovery and isolation of a receptor for interleukin-9, referred to as IL9R.

The IL9-R molecule is a glycoprotein which is characterized by a molecular weight of about 64 kilodaltons. Upon treatment with N-glycosidase F, the glycoprotein is digested to a peptide having a molecular weight of about 54 kilodaltons. Apart from binding to IL-9, the receptor may also be characterized in terms of its sources, which include IL-9 dependent cell line TS1. However, the activity of IL-9 on various cell types (Uyttenhove et al., Proc. Natl. Acad. Sci. USA 85: 6934 (1988); Van Snick et al., J. Exp. Med. 169: 363 (1989), Simpson et al., Eur. J. Biochem. 183: 715 (1989); Schmitt et al., Eur. J. Immunol. 19: 2167 (1989); Yang et al., Blood 74: 1880 (1989), suggests additional sources as well.

It has now been found by the inventors that IL-9 plays an important role in potentiating the effect that IL-4 has on the stimulation of IgG and IgE productions. This discovery, together with the discovery of a receptor for the IL-9 molecule itself, paves the way for a method of reducing the production of IgE in a subject. It is this, as well as a method for stimulating IgG production both in vitro and in vivo, in addition to a method for evaluating efficacy of anti-allergic treatment as well as a method for monitoring chronic diseases where abnormal IgE production is a feature that are the subjects of this invention.

DETAILED DESCRIPTION OF PREFERRED EMBODIMENTS

Example 1

Figure 1:
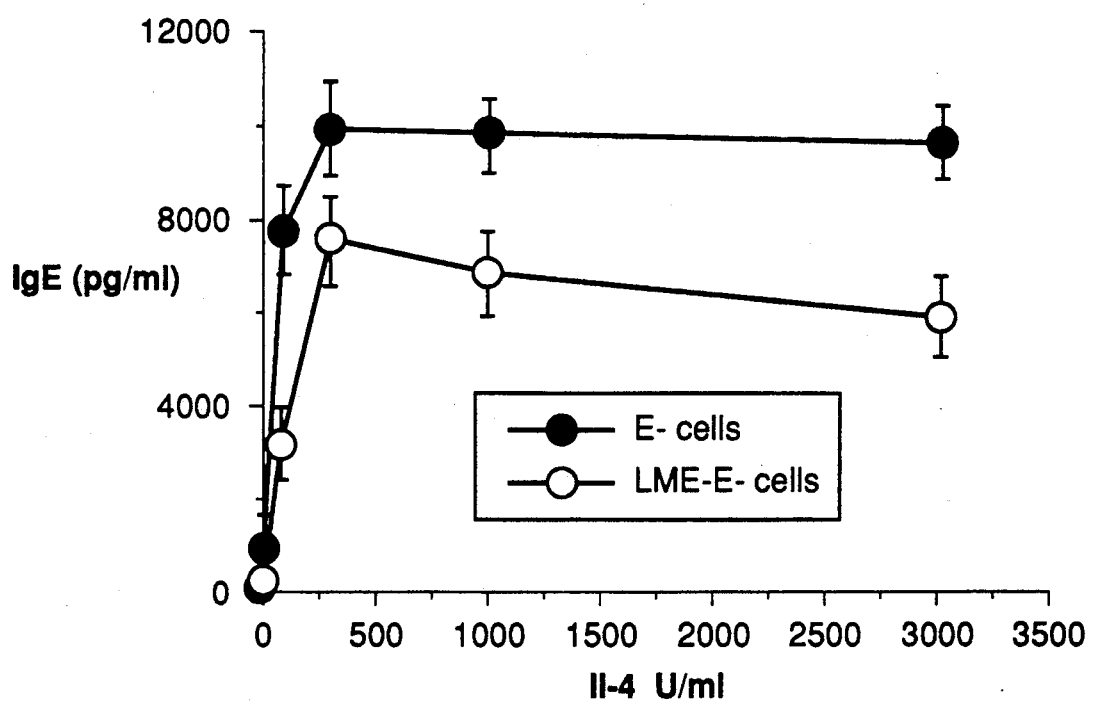
FIG. 1 shows the dose related effect of IL-4 on IgE production by normal human peripheral blood lymphocytes in vitro.
Figure 2A:
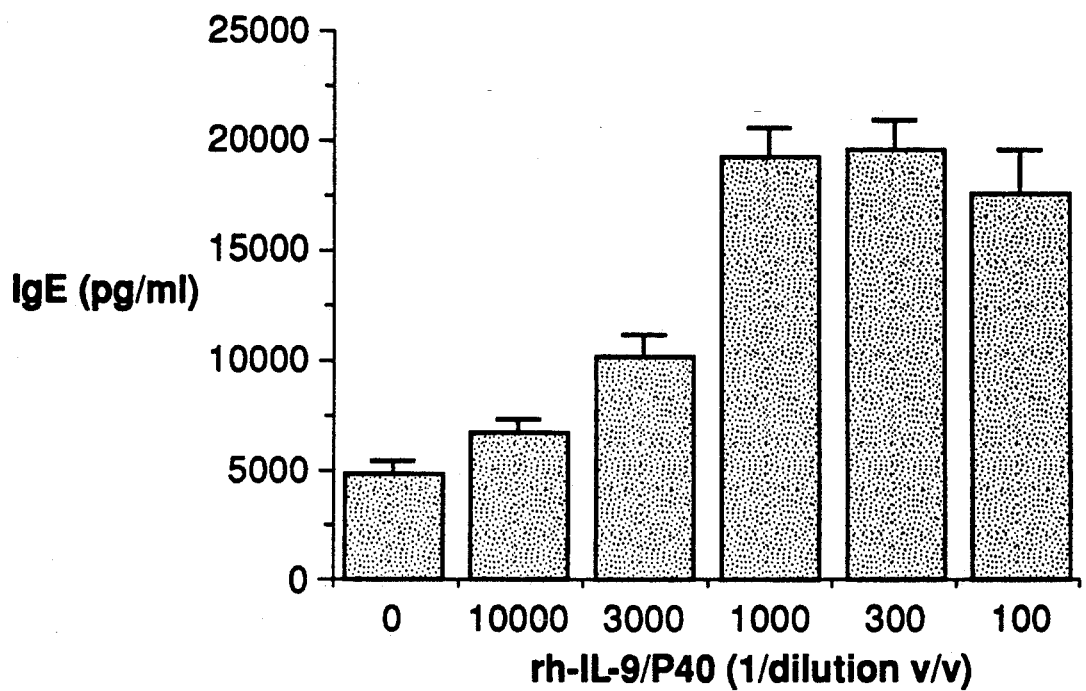
FIGS. 2a and 2b depict the effect of recombinant human and recombinant murine IL-9 on IL-4 induced IgE production by normal human peripheral blood lymphocytes in vitro.
Figure 2B:
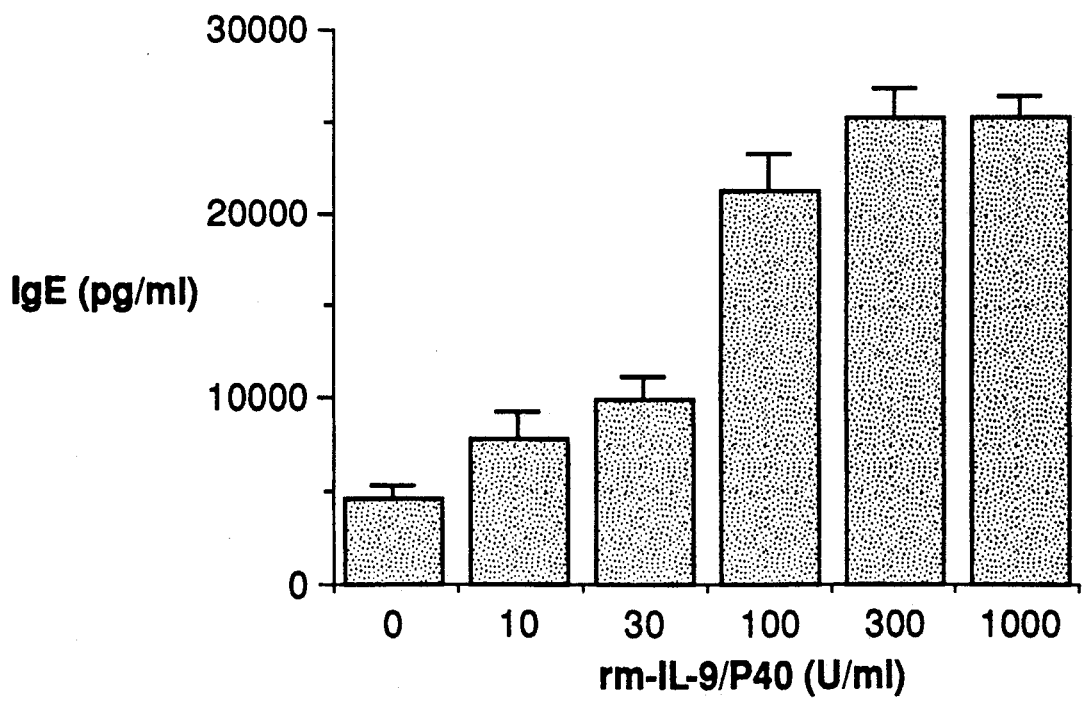

Cells and cell cultures were prepared as follows: Peripheral human blood lymphocytes (PBLs) were isolated from heparinized blood of healthy donors. The mononuclear cells were separated using Ficoll-/Hypaque gradient methodology, and monocytes were removed by incubating the PBLs with 5 mM L-Leucine methyl ester (LME) in serum RPMI medium for 45 minutes at room temperature, following Richard, et al., J. Immunol. 139: 1563 (1987). The thus treated population was washed twice, and is referred to hereafter as "LME-treated PBLs" or LME-treated E− cells.

Semi-purified B lymphocytes ("E− cells" hereafter) were obtained via rosetting once with neuraminidase treated sheep red blood cells, following plastic adherence for 1 hour at 37° C. When LME-treated PBLs were used, no plastic adherence was necessary.

In order to cause IgE production, the E− cells, which were found to contain 45% CD20+, 35% CD3+, and 10% CD14+ cells, or LEM-treated E− cells, which were 55% CD20+, 40% CD3+ and less than 1% CD14+ cells, were incubated at concentrations of $2 \times 10^6$ cells/ml in complete medium (RPMI 1640 medium supplemented with 10% heat inactivated FCS, 2 mM glutamine, 100 U/ml penicillin, 100 ug/ml streptomycin and 20 mM HEPES), at 37° C. in a 5% $CO_2$ humidified atmosphere, using different doses of interleukin 4 (30 or 300 U/ml) and/or doses of either recombinant human or recombinant murine IL-9 (1/100–1/10,000 v/v for the human variety and from 1 to 1000 U/ml of murine form). After 9–10 days of culture, cell free supernatants were collected, centrifuged (500 g, 10 minutes) and stored at −20° C. Example 2

Assays were carried out to measure production of IgE, IgG, and IgM. For IgE, flat bottomed microtiter plates were coated with rabbit anti-IgE, at 1:2000 dilution in bicarbonate buffer (pH 9.6), with overnight incubation at 4° C. After this, the plates were washed 4 times with phosphate buffered saline/0.05% Tween and were incubated for 1 hour with RPMI 1640/10% FCS at room temperature, so as to saturate protein binding sites. After washing, dilutions of culture supernatants and of IgE standards in PBS-Tween 0.05% were added to the plates. After 2 hours of incubation, plates were washed, and 200 ul dilute alkaline phosphatase-anti IgE conjugates (1:250) were added. Following 2 hours of incubation at room temperature, the plates were washed and 200 ul of p-nitrophenylphosphate in diethanolamine buffer was added. The plates were incubated at 37° C., and optical densities were measured at 405 nm using an autoreader. The sensitivity of this assay was 100 pg/ml.

To perform IgG and IgM assays, the same protocol was followed, except that plates were coated with either rabbit anti-human IgG (1:2000) or rabbit anti-IgM (1:1000), and the conjugates used were conjugates of IgG and alkaline phosphatase (ALP) or IgM-ALP. For IgG, following the ELISA, amounts of each Ig isosubtype were calculated using a computer connected in series. Sensitivities were ng/ml (IgG), and 2 ng/ml (IgM). When duplicate experiments were run, the standard deviation never exceeded 10% between samples.

The data show that when the E− cells were cultured in the presence of IL-4, IgE was produced in dose dependent manner after 9 days of culture. This is as predicted by Pene, et al., PNAS 85: 6880 (1988); Pene, et al., Eur. J. Immunol. 929 (1988), and Vercelli, et al., J. Exp. Med. 169: 1295 (1989). As shown by FIG. 1, a maximum effect is reached at 300 U/ml. Under these conditions, neither type of IL-9 used alone induced IgE synthesis even at the relatively high concentrations of 1/100 v/v for human and 1000 U/ml for murine forms. However, when less than optimal doses of IL-4 (100 U/ml) were used in connection with IL-9, IgE production was upgraded. This is a potentiating effect, seen to a much smaller degree, when the optimal dose of IL-4 (300 U/ml) was used. FIG. 1, and Tables I, II and III, which follow, set forth these data.

TABLE I

Effect of both human (h) and murine (m) IL-9 on Ig production by E cells.

| Challenge | IgG (ng/ml) | IgM (ng/ml) | IgE (pg/ml) |
|---|---|---|---|
| Medium | 85 ± 2 | 25 ± 3 | <100 |
| IL-4 | 195 ± 7 | 20 ± 1 | 4,775 ± 450 |
| h-IL-9 | 78 ± 5 | 24 ± 2 | <100 |
| m-IL-9 | 80 ± 2 | 19 ± 6 | <100 |

E cells were incubated with medium alone or an optimal dose of Il-4 (300 U/ml), h-IL-9 (1/1,000 v/v) or m-IL-9 (300 U/ml) for 9 days and the cell free supernatants were then assayed for their IgG, IgM and IgE content as described in materials and methods. The data represent the mean + SD of a duplicate experiment representative out of 3.

TABLE II

Effect of human (h) and mouse (m) IL-9 on IgE production by E− cells stimulated with an optimal dose of IL-4.

| Challenge | IL-4 (300 U/ml) | IgE (pg/ml) |
|---|---|---|
| Medium | − | <100 |
| Medium | + | 13,775 ± 675 |
| h-IL-9 | − | <100 |
| h-IL-9 | + | 17,456 ± 456 |
| m-IL-9 | − | <100 |
| m-IL-9 | + | 20,234 ± 389 |

E cells were cultured in medium alone or in medium containing 300 U/ml of Il-4 and were challenged or not with an optimal dose of either h-IL-9 (1/1,000 v/v) or m-Il-9 (300 U/ml). After 9 days of culture the cell free supernatants were assayed for their contents in IgE as described in materials and methods. The data represent the mean ± SD of a duplicate experiment representative out of three.

TABLE III

Effect of both human (h) and mouse (m) IL-9 on IL-4-induced IgE production by E and LME-treated E cells.

| Cells | IL-4 (100 U/ml) | Treatment | IgE (pg/ml) |
|---|---|---|---|
| E | − | Medium | <100 |
| E | − | h-IL-9 | <100 |
| E | − | m-IL-9 | <100 |
| E | + | Medium | 3,975 ± 556 |
| E | + | h-IL-9 | 18,776 ± 765 |
| E | + | m-IL-9 | 25,660 ± 456 |
| LME-E | − | Medium | <100 |
| LME-E | − | h-IL-9 | <100 |
| LME-E | − | m-IL-9 | <100 |
| LME-E | + | Medium | 1,395 ± 346 |
| LME-E | + | h-IL-9 | 9,996 ± 259 |
| LME-E | + | m-IL-9 | 11,567 ± 243 |

Cell populations from the same donor were incubated with medium alone or 100 U/ml of IL-4 in the presence or in the absence of h-IL-9/P40 (1/1,000 v/v) or of m-IL-9/P40 (300 U/ml). Culture supernatants were harvested after 9 days and assayed for their IgE concentration as described in materials and methods. The data represent the mean ± Sd of a duplicate experiment representative out of 3.

These data also provided insight into the effect of monocyte depletion on IL-4's role with respect to human B lymphocytes. Recently, it has been proposed that endogenous release of monocyte derived factors could potentiate the effect of IL-4 on B cells. See Dugas, et al., J. Lipid. Med. 2: 197 (1990), and Dugas, et al., Lipids, 1990 (in press). Thus, it was of interest to determine if IL-9 could potentiate IL-4 even after removal of monocytes and LME treatment. As Table III shows, IL-4 induced IgE production significantly decreased after LME treatment, but both forms of IL-9 still potentiated the effect. Thus, while the amount of IgE produced decreased, the IL-9 clearly potentiates production even in the absence of the monocytes.

Prior work had shown that IL-4 induces IgG production, but not IgM production. Pene, et al., Eur. J.

Figure 3:
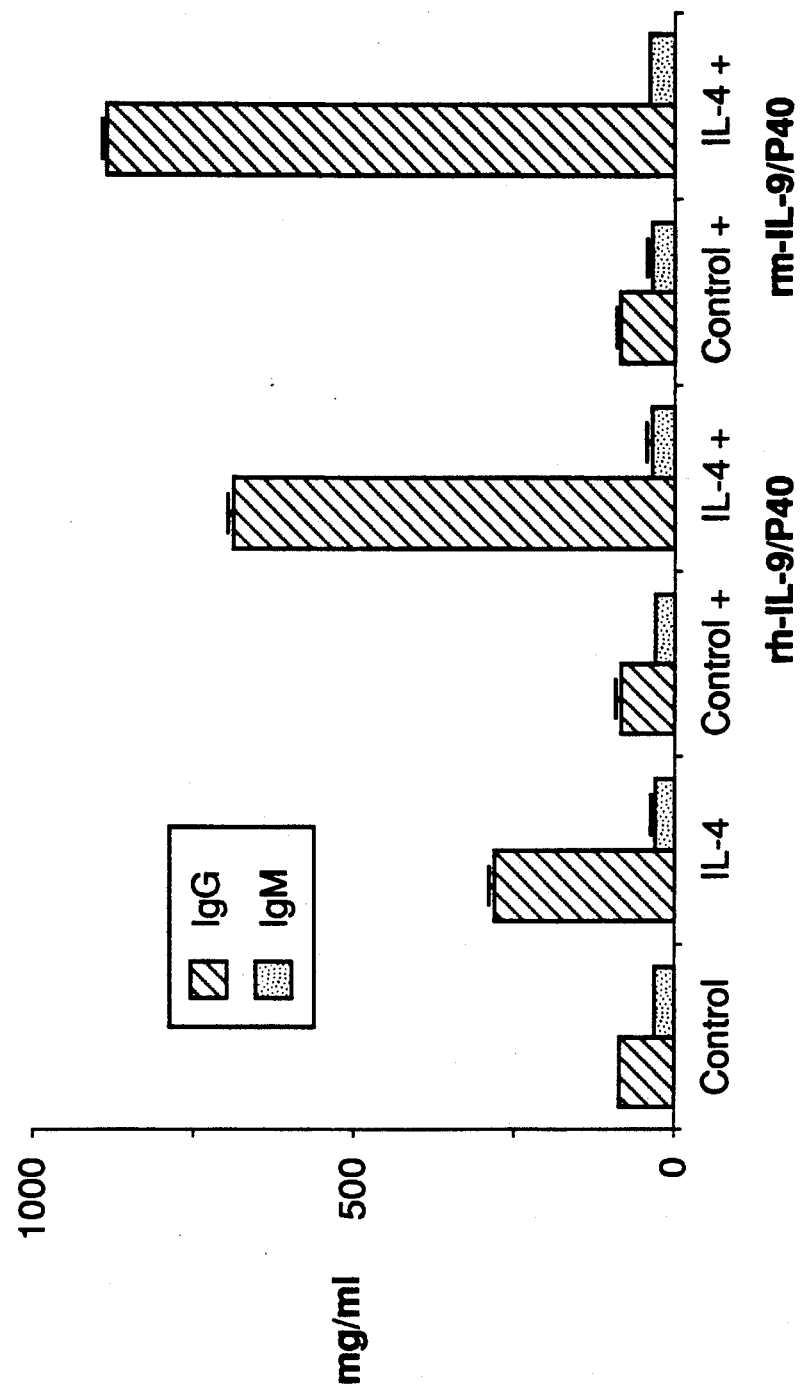
FIG. 3 presents data showing the effect of recombinant human and murine IL-9 on IL-4 induced IgG and IgM production by normal human peripheral blood lymphocytes.

Immunol. 18: 1929 (1988). The results shown in Table I, and FIG. 3 indicate agreement with the earlier studies as to IL-4's effect on IgG and IgM and show that IL-9, which had no effect on Ig by itself, did potentiate IgG with IL-4, but had no effect on IgM.

These results show that a combination of IL-4 and IL-9 can be used to increase the production of IgG by antibody producing cells. This is important not just for in vivo types of treatment, but also for cell culture such as hybridoma culture, or culture of other antibody producing cells, where IgG production is important. Thus, the invention relates not only to a method for potentiating the IgG response in an animal such as a human, but also to the enhancement of IgG production in vitro, by adding IL-4 and IL-9 together in an amount sufficient to potentiate the IgG production of the cells. The amount will vary; however, as has been shown, desirably the amount of IL-4 is a concentration of less than about 300 U/ml, preferably about 100 U/ml, while the amount of IL-9 used varies. A preferred amount is about 300 U/ml when murine IL-9 is used, and a concentration of about 1/1000 (v/v) when human IL-9 is used. The form of the cytokine used may be the naturally occurring molecule, or the recombinant form, the latter type being especially preferred. In connection with the inhibition of IgE production, again the amount of inhibitor may vary, depending on the material used, soluble receptor for IL-9 ("IL-9R"), e.g., is preferably used in a range of from about 10 μg/kg to about 250 μg/kg, preferably about 100 μg/kg of the subject. Other inhibitors, such as anti-receptor antibodies and other antigonists may be administered in amounts ranging from about 5 mg/kg to about 200 mg/kg, preferably 10 to about 100 mg/kg. "Kg" of course, refers to the body weight of the subject.

The effect of IL-9 on potentiating IgE production also leads to a method for reducing or suppressing this production. The IL-9 molecule is known to require interaction with a receptor, i.e., "IL-9R" in order to exert any effect on the cell. To that end, the effect of IL-9 on cells may be reduced or eliminated by administering an inhibitor in an amount sufficient to reduce or eliminate the IgE potentiating effect. Such an inhibitor may be, e.g., an antibody against IL-9 or soluble IL-9R receptor. When "antibody" and "receptor" are used herein, they embrace not only the whole antibody or whole receptor, but also fragments of these molecules sufficient to react with and inhibit the IL-9. Other inhibitors will be recognized by the skilled artisan.

In addition, given the observation that IL-9 is produced during an allergic response the efficacy of anti-allergy therapy may be determined by measuring IL-9 content of a sample, and relating this measurement to a given standard. Increases or decreaes over that standard would be reflective of the status of anti-allergic therapy.

The terms and expressions which have been employed are used as terms of description and not of limitation, and there is not intention in the use of such terms and expressions of excluding any equivalents of the features shown and described or portions thereof, it being recognized that various modifications are possible within the scope of the invention.

We claim:

1. Method for inhibiting IgE production comprising administering to a subject an amount of an interleukin 9 inhibitor selected from the group consisting of an antibody which specifically binds to interleukin 9, a soluble interleukin 9 receptor, and an antibody which specifically binds to interleukin 9 receptor sufficient to inhibit production of IgE.

2. Method of claim 1, wherein said interleukin 9 inhibitor is an antibody which specifically binds to interleukin 9.

3. Method of claim 1, wherein said interleukin 9 inhibitor is soluble interleukin 9 receptor.

4. Method of claim 1, further comprising administering an interleukin 4 inhibitor selected from the group consisting of an antibody which specifically binds to interleukin 4, a soluble interleukin 4 receptor, and an antibody which specifically binds to interleukin 4 receptor to said subject.

5. Method of claim 4, wherein said interleukin 4 inhibitor is an antibody which specifically binds to interleukin 4.

6. Method of claim 4, wherein said interleukin 4 inhibitor is soluble interleukin 4 receptor.

7. Method of claim 1, wherein said interleukin 9 inhibitor is an antibody which specifically binds to interleukin 9 receptor.

8. Method of claim 4, wherein said interleukin 4 inhibitor is an antibody which specifically binds to interleukin 4 receptor.

* * * * *